United States Patent [19]

Seo

[11] Patent Number: 4,663,091
[45] Date of Patent: May 5, 1987

[54] HUMIDIFIER FOR REMOVING BACILLI FROM WATER

[75] Inventor: Sun K. Seo, Seoul, Rep. of Korea

[73] Assignee: Sam Sung Electronic Co., Ltd., Suwon, Rep. of Korea

[21] Appl. No.: 789,844

[22] Filed: Oct. 21, 1985

[30] Foreign Application Priority Data

Oct. 23, 1984 [KR] Rep. of Korea ............... 1984-6595

[51] Int. Cl.$^4$ .............................................. B01F 3/04
[52] U.S. Cl. ............................ 261/72.1; 210/748; 261/81; 261/DIG. 48; 261/DIG. 46; 261/DIG. 80
[58] Field of Search ............... 210/748; 261/DIG. 48, 261/DIG. 46, 72 R, 81, DIG. 80

[56] References Cited

U.S. PATENT DOCUMENTS

| | | | |
|---|---|---|---|
| 3,236,757 | 2/1966 | Litt | 210/748 |
| 3,776,530 | 12/1973 | Griffith et al. | 261/DIG. 46 |
| 4,087,495 | 5/1978 | Umehara | 261/DIG. 48 |
| 4,157,963 | 6/1979 | Jessop et al. | 261/DIG. 46 |
| 4,257,989 | 3/1981 | Nishikawa | 261/DIG. 46 |
| 4,367,132 | 1/1983 | Bell et al. | 210/748 |
| 4,552,664 | 11/1985 | Benner | 210/748 |

FOREIGN PATENT DOCUMENTS

| | | | |
|---|---|---|---|
| 3511887 | 10/1985 | Fed. Rep. of Germany | 261/DIG. 48 |
| 53-108654 | 9/1978 | Japan | 210/748 |
| 54-56236 | 5/1979 | Japan | 261/DIG. 48 |

Primary Examiner—Tim Miles
Attorney, Agent, or Firm—Watson Cole Grindle & Watson

[57] ABSTRACT

A humidifier for sterilizing bacilli by alteration of the alkalinity of water in a water tank to sterilize it and automatically remove scale on the internal walls of the water tank. The humidifier includes a base housing with spaced first and second electrical terminals, first and second recesses with a pin projecting therefrom and an aperture. A vibrator spray section emits moisture and is connected to the first recess through the aperture. The water tank is removably mounted onto the base housing and includes a porous divider for dividing the tank into substantially equal sections each including first and second valve members respectively engageable with the first and second recesses. Cavities in the bottom of the tank have electrodes mounted thereon for accommodating the first and second electrical terminals. Each of the valve members includes a spring-biased valve closing an aperture in the tank with the first valve member engaging the pin to open the first valve and the second valve being received in the second recess whereby the second valve is closed with the water tank mounted on the base housing.

3 Claims, 3 Drawing Figures

HUMIDIFIER FOR REMOVING BACILLI FROM WATER

BACKGROUND OF THE INVENTION

The present invention relates to humidifier apparatus for sterilizing bacilli and more particularly to such a humidifier for altering the alkalinity of water in the water tank to completely sterilize it and to automatically remove scale on the internal wall of the water tank to extend the life of the spray elements including the vibrator and other elements of the humidifier.

Humidifiers of the type disclosed herein are commonly used in rooms for a baby, infant, patient, the old and infirm to maintain the moisture of the room at a given level. However, there is considerable concern relating to the introduction of diseases, and especially infectious diseases, because the jets of moisture emitted by the humidifier are not completely sterilized to remove any bacillus contained therein.

In humidifiers of the type specified herein, water is ordinarily essentially vaporized and then sprayed into the atmosphere through a nozzle by a rotating vibrator element. Thus, as the water in the humidifier tank contains a large quantity of bacilli, the water jetted from the nozzle will contaminate the air in the room with the bacilli present in the water. The inhalation of such contaminated air by the patient can result in the patient being infected by the bacilli. Moreover, the bacilli in the water tank of the humidifier may also contaminate the internal walls thereof as well as the vibrator, which contamination further contributes to the fouling of the air in the room when the humidifier emits moisture. Additionally, the transparent water tank becomes unsightly when the contaminated water adheres to its internal sides. The accumulation of contaminants on the various parts of the humidifier, and particularly the vibrator, causes a loss in the effectiveness of the humidifier to dispense moistened water, as well as to shorten the life of the humidifier.

Aside from the undesireable spreading of contaminants by means of the moistened water emitted from the humidifier, the contamination in the form of "fur" adhering to the various elements of the humidifier necessitates that the inside of the humidifier and its various components require frequent cleaning.

SUMMARY OF THE INVENTION

For the purpose of solving the aforementioned problems the humidifer of the present invention uses a porous material to separate the water tank into two equal parts and provides a positive and a negative electrical bias to respective portions of the water tank, thereby enabling the water in the water tank to be sterilized. Furthermore, the water tank is constructed with transparent side walls and a top so that the water can be seen. The water tank is also constructed such that each of the two portions are symmetrical and each section is provided with a spring-loaded valve whereby water is emitted from only one section of the tank at a time. The water tank is symmetrical and can be removed and rotated one hundred eighty degrees so that the water in the other section is emitted to the vibrator to be sprayed from the humidifier.

A significant feature of the invention relates to the construction of the water tank and more particularly to the spring-loaded valves thereof for enabling purified water to selectively flow from the water tank to the vaporizing and spray element. The base housing upon which the water tank rests is so configured that water only flows from the valve in the water tank that is positioned in the section thereof containing the negative electrical terminal.

BRIEF DESCRIPTION OF THE DRAWINGS

The above advantages, features and objects of the invention are readily apparent from a consideration of a preferred embodiment of the best mode of carrying out the invention as set forth in the following description when taken in conjunction with the drawings wherein.

DETAILED DESCRIPTION OF THE PREFERRED EMBODIMENT

Figure 1:
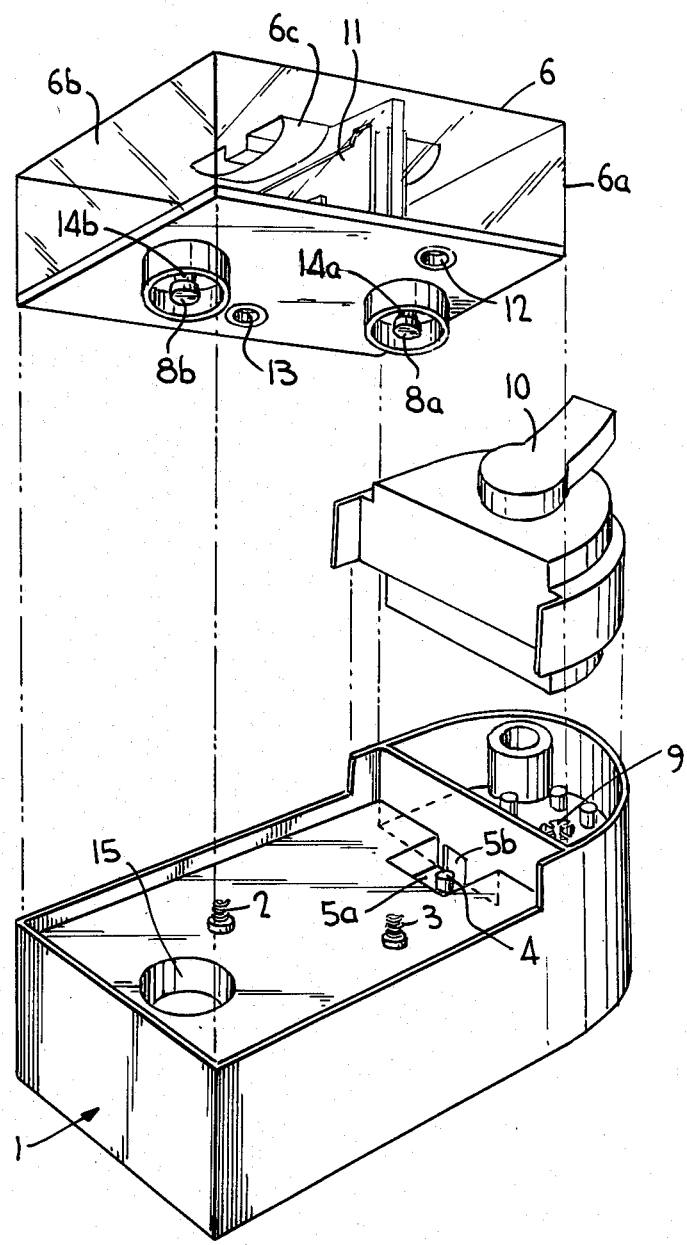
FIG. 1 illustrates an exploded perspective view of the humidifier in accordance with the invention.
Figure 2:
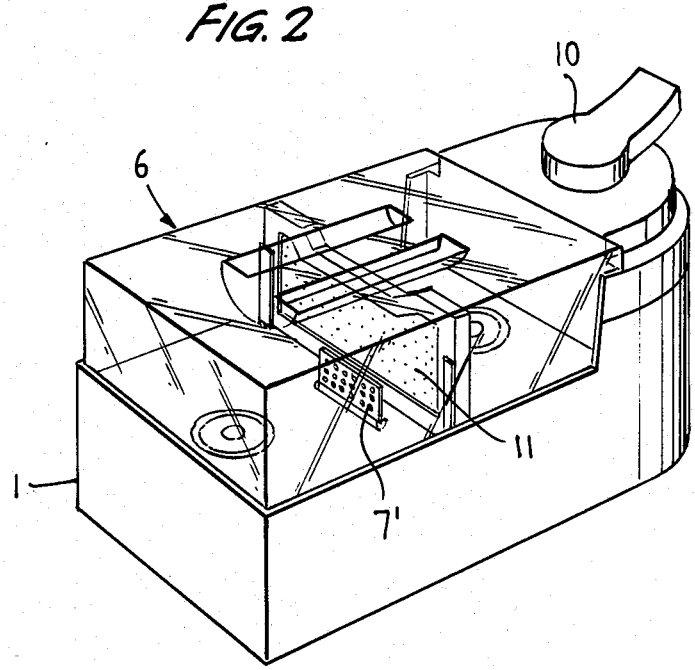
FIG. 2 is a perspective view of the assembled humidifier in accordance with the invention.
Figure 3:
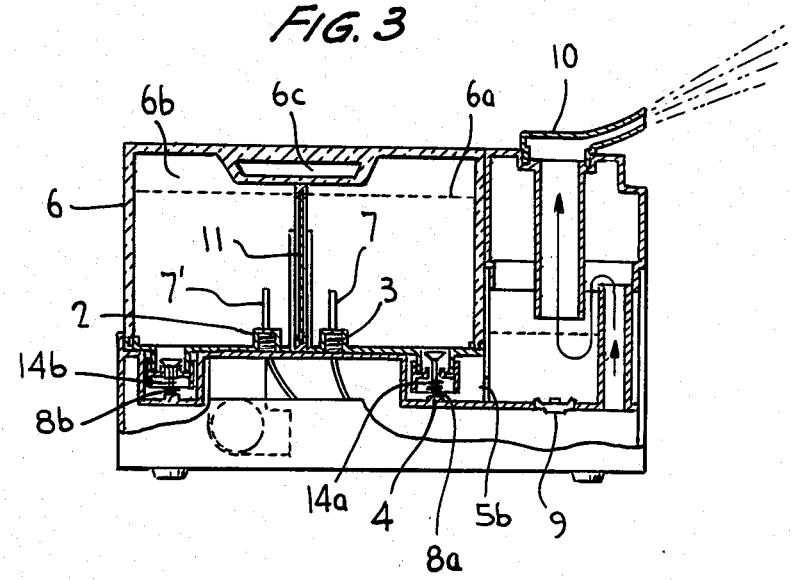
FIG. 3 is a sectional view through the longitudinal axis of the humidifier showing the relationship of the significant elements thereof.

As illustrated in FIGS. 1 and 3, base housing 1 of the humidifier includes a positive terminal 2 and a negative terminal 3, which are respectively placed to be in opposite sections of the water tank portion 6 of the humidifier. Vibrator 9 is mounted in the bottom of the front jet section of the humidifier including rotatable nozzle 10 which emits moistened water vapor when the vibrator rotates. The vibrator and nozzle section of the humidifier are made in a conventional manner.

Terminals 2 and 3 are respectively connected to the positive and negative terminals of an appropriate DC voltage source (not shown) contained in the base housing 1, which may include a rectifier such that the necessary DC voltage is provided from the rectified conventional power main source such as 115 or 230 volts. Upstanding pin 4 is formed at the bottom of recess 5a which is aligned with one of the water valve outlets 8a, 8b of the water tank 6. Recess 5a includes an opening 5b into the front nozzle section of the humidifier. In a manner to be described more fully hereinafter, when the water tank 6 is mounted on the base housing 1, water is allowed to flow from the water tank 6 into recess 5a and then through port 5b into the front nozzle section where rotation of the vibrator 9 causes heated, moistened vapor to be emitted from nozzle 10 in a manner known to those skilled in the art of humidifiers.

Water tank portion 6 includes two spring-loaded valve members 8a and 8b each respectively mounted in the bottom surface of the tank 6 and each including a respective spring member 14a, 14b which causes each respective valve member 8a or 8b to be normally closed. The bottom portion of tank 6 also includes respective cavities 12 and 13 engaging electrical terminals 2 and 3 of tank 6 when it is mounted on base housing 1 as illustrated in FIG. 3. Housing 6 is divided into two equal sections 6a and 6b by perforated porous member 11. The positive terminal 2 protrudes into cavity 13 in portion 6a and negative terminal 3 protrudes into cavity 12 in portion 6b as is illustrated in FIG. 3. Water tank 6 also includes recessed handle portion 6c formed in the top of the water tank to enable it to be readily grasped to be placed on, and removed from, the base of housing 1. Water tank 6 is constructed so that it may be lifted from base housing 1 and rotated one hundred eighty degrees and then placed on top of base housing 1 such that the electrodes 2 and 3 are respectively positioned within portions 6c and 6b, e.g. in the reverse manner and rotated one hundred eighty degrees.

When the water tank 6 is mounted on the base housing 1, the valve 8a engages pin 4 and is opened to allow water to egress from portion 6b of the water tank as is illustrated in FIG. 3. The other valve member 8b is closed by the force of spring 14b as that valve member is positioned within recess 15 in base housing 1.

Base housing 1 also includes a circular recess 15 for accommodating that valve member 8b in the respective section of the water tank 6 that is positioned thereover when tank 6 is mounted onto base housing 1 such that the valve member 8b remains in its normally closed position by the force of spring 14b (see FIG. 3).

The water tank 6 is filled with water by lifting the tank from base housing 1, inverting it and unscrewing the respective valve 8a, 8b and pouring water into each section 6b and 6c of tank 6.

When an ON/OFF switch (not shown) is switched to the "on" position, an electric current flows between the positive electrode 7 and the negative electrode 7' (FIG. 3) as the water in tank 6 is ionized The electrolysis involves the flow of metallic ions ($Ca++$, $Mg++$, $Na++$) which are dissolved in the water to the negative electrode 3 through porous partition 11. Also cathodic ions ($Cl^{-3}$), also dissolved in the water, move to the positive electrode 7 through the partition 11. The resulting electrolysis of the water causes the negative terminal 7' side to become alkaline and the positive terminal to become acidic.

From the foregoing description it is evident that a significant feature of the invention is the provision of valve mechanisms in the humidifier water tank and the respective coacting pin 4 and recess 15 in the base housing 1 for respectively actuating valve member 8a and not activating valve member 8b with water tank 6 mounted on base housing 1. By virtue of such a construction water can only egress from the acidic portion of the water in tank 6 regardless of which section 6b or 6c of the water tank 6 is positioned next to the vibrator 9 of the humidifier.

The construction and operation of the spray section including vibrator 9 of the humidifier is so well known to those skilled in the humidifier art that no detailed description of such structure is required to enable the present invention to be practiced.

Similarly, no further description is necessary of the voltage applied to each of terminal electrodes 2 or 3 as such is known to those skilled in the humidifier art.

Those skilled in the humidifier art will recognize that there are many variations of the invention and that the invention is to be limited only by the following claims and the equivalents to which the various elements thereof are entitled.

What I claim is:

1. A humidifier, comprising:
   a base housing, comprising first and second spaced electrical terminals, first and second recesses, said first recess including a pin projecting therefrom and an aperture, and a vibrator spray section for the emission of moisture and connected to said first recess through said aperture; and
   a water tank adapted to be mounted onto said base housing and comprising a porous divider dividing said water tank into two equal sections each including first and second valve members respectively engageable with said first and second recesses with said water tank mounted onto said base housing, first and second cavities in the bottom of said tank having electrodes mounted thereon for accommodating said first and second electrical terminals, each of said valve members including a springbiased valve member closing an aperture in said tank, said first valve member engaging said pin to open said first valve member and said second valve member being received in said second recess whereby said second valve member is closed with said water tank mounted onto said base member.

2. A humidifier as claimed in claim 1 wherein said water tank includes a transparent top with a recessed handle therein.

3. A humidifier as claimed in claim 1 wherein said water tank is symmetrical such that it can be mounted onto said base housing with said first and second valve members rotated by one hundred eighty degrees.

* * * * *